United States Patent
Hell

(10) Patent No.: US 7,115,885 B2
(45) Date of Patent: Oct. 3, 2006

(54) METHOD AND DEVICE FOR MULTI PHOTON EXCITATION OF A SAMPLE

(75) Inventor: Stefan Hell, Göttingen (DE)

(73) Assignee: Max-Planck-Gesellschaft zur Förderung der Wissen-schaften e.V., München (DE)

(*) Notice: Subject to any disclaimer, the term of this patent is extended or adjusted under 35 U.S.C. 154(b) by 142 days.

(21) Appl. No.: 10/684,115

(22) Filed: Oct. 10, 2003

(65) Prior Publication Data

US 2004/0114138 A1    Jun. 17, 2004

Related U.S. Application Data

(63) Continuation-in-part of application No. PCT/EP02/03785, filed on Apr. 5, 2002.

(30) Foreign Application Priority Data

Apr. 12, 2001  (DE) ............... 110 11 8355

(51) Int. Cl.
  *G41B 9/02*  (2006.01)
(52) U.S. Cl. .............. 250/459.1; 356/35.5; 356/318
(58) Field of Classification Search ............ 250/459.1, 250/458.1, 215; 356/349, 35.5
See application file for complete search history.

(56) References Cited

U.S. PATENT DOCUMENTS

| 6,020,591 A |   | 2/2000 | Harter et al. ............ 250/458.1 |
| 6,028,686 A | * | 2/2000 | Mirell ........................ 398/201 |
| 6,107,637 A | * | 8/2000 | Watanabe ................ 250/559.3 |
| 6,262,423 B1 | * | 7/2001 | Hell ........................ 250/458.1 |

FOREIGN PATENT DOCUMENTS

CH    678108 A5 *  7/1991

* cited by examiner

*Primary Examiner*—Thanh X. Luu
*Assistant Examiner*—Tony Ko
(74) *Attorney, Agent, or Firm*—Thomas, Kayden, Horstemeyer & Risley LLP

(57) ABSTRACT

In a method for multi photon excitation of a sample a laser beam is split into at least two coherent partial beams each having a beam axis and a same intensity distribution about its beam axis. The partial beams are directed from different directions towards a common measuring plane running transversely to the beam axes at an inclination angle <1 between the beam axes of the partial beams; and the partial beams are projected onto the measuring plane by means of a common lens system. Thus, an interference pattern formed by the coherent partial beams within the measuring plane provides areas of maximum light intensity adjacent to areas of minimum light intensity.

12 Claims, 2 Drawing Sheets

METHOD AND DEVICE FOR MULTI PHOTON EXCITATION OF A SAMPLE

CROSS REFERENCE TO RELATED APPLICATIONS

This application is a continuation in part of International Patent Application PCT/EP02/03785 filed Apr. 5, 2002 and claiming priority to co-pending German Patent Application No. 101 18 355.0-42 filed Apr. 12, 2001 both of which are entitled "Verfahren und Vorrichtung zur Mehrphotonenanregung einer Probe".

FIELD OF THE INVENTION

The present invention generally relates to a method for multi photon excitation of a sample, comprising the steps of splitting a laser beam into at least two coherent partial beams each having a beam axis and a same intensity distribution about its beam axis, directing the partial beams in different directions, and projecting the partial beams from different directions onto a common measuring plane running transversely to the beam axes, an interference pattern being formed by the coherent partial beams in the area of the measuring plane.

Further, the invention relates to a device for multi photon excitation comprising a laser providing a laser beam, a beam splitter splitting the laser beam into at least two coherent partial beams each having a beam axis and a same intensity distribution about its beam axis, beam directing means directing the partial beams in different directions, and projecting means projecting the partial beams from different directions onto a common measurement plane running transversely to the beam axes, an interference pattern being formed by the coherent partial beams in the area of the measuring plane.

PRIOR ART

Multi photon excitation of a sample in a measuring point is, for example, accomplished in scanning microscopes in which a particularly high spatial resolution is to be obtained. In case of a two photon excitation of a sample, the intensity distribution of the fluorescence light emitted by the sample is proportional to the third power of the intensity distribution of the excitation light. Thus the effective spatial resolution can be increased with a limited minimum full width of half maximum of the intensity distribution of the excitation light in each measuring point by means of analyzing the fluorescence light from a multi photon excitation.

It is a disadvantage of multi photon excitation of a sample that the intensity of the fluorescence light, because of its dependency on a power of the intensity of the excitation light described above, is often only very small with smaller intensity of the excitation lights avoiding damages to the sample, and thus requires longer measuring times. In a method and a device of that types described at the beginning which are known from DE 196 53 413 A1, it is accounted for this disadvantage by exciting the sample in a plurality of measuring points located side by side in the measuring plane at the same time. This is accomplished in that an incoming laser beam is directed onto a micro lens array and is thus focused in a multitude of focus points of the single micro lenses arranged side by side. These focus points are then projected by a projection system into measuring points in the measuring plane. In this context, DE 196 53 413 A1 also discloses embodiments of the method and the device in which the single micro lenses of the micro lens array have different positions along the beam axis and/or different focal lengths. Thus, the measuring points are arranged at different depth within the sample to scan the sample also in depth direction. These arrangements, in which the measuring points do not exactly fall within one geometric plane shall be included, when a "plurality of measuring points which are arranged side by side within one measuring plane running transversely to the respective beam axis" is mentioned here.

The embodiments of DE 196 53 413 A1 which correspond to the method and the device of the types described at the beginning split the laser beam into two partial beams of a same intensity distribution about their respective beam axes, after the laser beam has been directed onto the micro lens array and was thus distributed over a plurality of focus points arranged side by side. These partial beams are then focused into the measuring points within the measuring plane out of two diametrically opposing directions, i.e. towards the front and towards the back of the sample, by means of two lens systems. Because of the coherence of the partial beams a interference pattern results in each of the measuring points, the areas of maximum and minimum intensity showing a sequence in the direction of the beam axes. Particularly, a main maximum in which an essential excitation of the sample occurs is formed in the measuring plane directly about the geometric measuring point. The side maximums located in front and behind the measuring plane are only of minor importance, simply because of the intensity distribution of each partial beam about the measuring point, so that they do not relevantly contribute to a multi photon excitation of the sample. In this way, the depth resolution is enhanced in multi photon excitation of the sample. The overall construction required for this enhancement is, however, comparatively complicated as the division of the laser beam into two partial beams of the same intensity distribution extends up to the sample. I.e., there is one optical system for each partial beam, and these two optical systems have to be fine adjusted with regard to each other. Additionally, a sample slide and holder have to permit that the two partial beams enter the sample from two opposite directions.

To the end of making an as good as possible use of the light power of the laser beam provided by a laser, the single micro lenses of the micro lens array according to DE 196 53 413 A1 are as close to each other as possible so that no portions of the laser beam are blocked.

A plurality of measuring points located side by side in the measuring plane, the sample being exited with about the same intensity via a multi photon process in each of which, is not always without problems with the known methods and the known devices. There are samples having a strongly differing local sensitivities with regard to the exiting light. Thus, with an uniform intensity distribution over the different measuring points, a sample may already be damaged by the excitation light in some of the measuring points, while in other measuring points there is not yet a suitable intensity of fluorescence light.

DE 198 51 240 C1 discloses a fluorescence microscope with multi photon excitation in which a spatial limitation to the multi photon excitation is achieved in that different parts of the incident light are directed into a common focal point under incident directions intersecting each other at a larger angle. This results into an intersection volume clearly smaller than the single volumes which are illuminated by one of the parts of the incident light only and which are each elongated in the light incident direction. The actual multi photon excitation is limited to that intersection volume. An interference of the single parts of the incident light is not considered in DE 198 51 240 C1. Indeed, they have different wave lengths. The angle, at which the light incident directions intersect is in the area of about 90°. As an additional and separate measure in certain embodiments of the known fluorescence microscope, it is intended that the light incident directions are diametrically opposing each other in the focal points so that the parts of incident light interfere and form an interference pattern along the opposing light incident directions. This corresponds to that part of the disclosure of DE 196 53 413 A1 discussed above which is regarded as the most relevant prior art.

BACKGROUND OF THE INVENTION

The invention is based on the task to provide a method and a device of the types described at the beginning which make use of a given intensity of a laser beam for multi photon excitation of a sample in an optimized way.

SUMMARY OF THE INVENTION

The present invention provides A method for multi photon excitation of a sample, comprising the steps of splitting a laser beam into at least two coherent partial beams each having a beam axis and a same intensity distribution about its beam axis; directing the partial beams from different directions towards a common measuring plane running transversely to the beam axes at an inclination angle <1 between the beam axes of the partial beams; and projecting the partial beams onto the measuring plane by means of a common lens system, an interference pattern formed by the coherent partial beams within the measuring plane providing areas of maximum light intensity adjacent to areas of minimum light intensity.

The value of the inclination angle which has to be smaller than 1 is its circular measure by radians. I.e. the limit of 1 corresponds to $360°/2\pi$ which is about 57°.

In the new method, the partial beams are not caused to interfere in the area of the measuring plane out of diametrically opposed directions. Instead, the partial beams the number of which may also be higher than 2 originate from essentially the same direction, only the small inclination angle of less than 1 being between them. This results into an interference pattern in which the areas of maximum and minimum intensity do not show a sequence in the direction of the depth of the sample but in the measuring plane, and particularly in the direction of the inclination angle. The distance of the areas of maximum intensity within this interference pattern depends on the inclination angle and also on the optical data of the lens system. Thus, this distance can be adjusted as desired. Independently of this distance, the method according to the invention always has the advantage that the utilization of a given intensity of the laser beam is improved because an inhomogeneous intensity distribution is provided in the measuring plane by means of the interference pattern. The resulting better utilization of the provided light power of the excitation light is based on the non-linearity of the fluorescence light yield in a multi photon excitation. Considering, for example, a two photon excitation, an interference pattern which distributes an average relative intensity of 1 over areas of a relative intensities of 2 and 0 results in a relative excitation of $2^2=4$ in the areas of the relative intensity of 2. As the portions of the areas of both relative intensities are the same, this corresponds to an average excitation of 2. In case of the original intensity, an average excitation of $1^2=1$ is achieved only. Although the intensity distribution of the excitation light on which this example is based is just theoretic, the example nevertheless shows the potential of the present invention. In other words, the interference pattern in the measurement plane improves the relative yield of fluorescence light in a multi photon excitation per se. This effect is even more prominent in case of a three photon excitation or in a process in which even more photons are involved. The above stated points apply independently of whether the intensity distribution of the excitation light caused by the interference pattern in the measurement plane is resolved or not in observing the fluorescence light from the sample.

A lateral offset of the partial beams in the measurement plane caused by the inclination angle should always be < 50% of the full width at half-maximum (FWHM) of the intensity distribution of each partial beam in the measuring plane. A lateral offset of the partial beams in the measuring plane which is 25% of this FWHM at maximum is even more preferred.

Focusing the partial beams in at least one common measuring point within the measuring plane is not necessary for utilizing the general advantages of the new method with regard to the fluorescent light yield but it is nevertheless useful for utilizing the possibility of realizing a high spatial resolution in multiple photon excitation of the sample.

Because of the comparatively small inclination angle between the axes of the partial beams it is very useful to split the laser beam into the partial beams prior to any further beam formation, i.e. particularly prior to dividing the partial beams onto a plurality of focal points arranged side by side by means of a micro lens array, for example, to then project these focus points into the measuring points.

Besides the general advantage of the intensity distribution of the interference pattern in the measuring plane described above, particular advantages can be achieved in that the distance of the areas of maximum intensity in the interference pattern is at least half as wide as the distance of the measuring points. Thus, on the one hand, the single measuring point can fully utilize the increased relative yield of fluorescence light. On the other hand, it is possible to excite areas of different sensitivity of a sample with excitation light of different intensity by means of the intensity distribution of the interference pattern.

If it is not useful or necessary with a particular sample to excite different areas of a sample with different intensities of excitation light, the phase of at least one of the partial beams can be modulated by varying its path length so that the areas of maximum intensity of the interference pattern are moved forth and back in the measuring plane. It is not necessarily the sense of this measure to scan the sample with the interference pattern but to uniformly distribute the exciting light intensity. Because of the non-linearity of the multi photon excitation there is nevertheless an improved utilization of the provided light intensity, i.e. input light power, of the laser beam as it has been described above in the context of fine interference patterns. The invention also provides a device for multi photon excitation comprising a laser providing a laser beam, a beam splitter splitting a laser beam into at least two coherent partial beams each having a beam axis and a same intensity distribution about its beam axis, beam directing means directing the partial beams from different directions towards a common measuring plane running transversely to the beam axes at an inclination angle <1 between the beam axes of the partial beams, and a common lens system projecting the partial beams onto the measuring plane, an interference pattern formed by the coherent partial beams within the measuring plane providing areas of maximum light intensity adjacent to areas of minimum light intensity.

The beam directing means may include a roof mirror joining the partial beams which are directed towards the roof mirror from opposite directions at its roof ridge. For implementing the invention, it is however only important, that two partial beams with about a same intensity distribution are provided, and that these can be oriented at a small inclination angle with regard to each other. This can also be achieved by other optical means well known to those skilled in the art.

Thus, for example, the beam splitter and the beam directing means can both be formed by one optical element. For example, the optical element may have an active surface made of micro mirrors which in groups are inclined against each other. Such optical elements are available from Texas Instruments, USA. The micro mirrors may, for example, be divided up and controlled in two groups arranged like the fields of a chessboard: each the "black" and the "white" fields or micro mirrors have a same orientation and together form one of the partial beams of the laser beam.

The optical element may, however, also have an active transmission area which is comprised of groups of different or differently operated micro delay plates. Optical elements having electronically operated liquid crystal delay segments are, for example, available from DisplayTech USA. An arrangement of two groups of the micro delay plates for forming the two partial beams may here also be like a chessboard. Although optical elements with liquid crystal delay segments up to now only have a comparatively small transmission, it will be seen that they will be a future first choice in the realization of the present invention as soon as they have enhanced transmission values.

The lens system may comprise a micro lens array made of a plurality of micro lenses arranged side by side in one plane for distributing the partial beams over a plurality of focal points. In general, it is also possible to make use of other possibilities like a multiple aperture to this end. However, all apertures have the drawback that the incident beam of light or the incident partial beams are partially blocked so that valuable light power is lost.

In using a micro lens array an upper limit for the inclination angle should be smaller than Lambda (M*NA*f), Lambda being the wavelength of the laser beam and the partial beams, M being the magnification upon focusing the partial beams into each measuring point, NA being the numeric aperture of the lens systems, and f being the focal length of each micro lens of the micro lens array. Typical values of lambda are between 0,004 and 0,0015 mm. Typical values of M are between 0,05 and 0,01. Typical values of NA are between 0,2 and 1,6; and typical values of f are between 1 and 20 mm. This results into an inclination angle which can be smaller than $0,25*10^{-3}$ and which is typically $\leq 1,0*10^{-3}$.

The beam directing means may comprise at least one deviation element which modulates the phase of at least one of the partial beams by varying its paths length. This deviation element can, for example, be a mirror supported by an piezo element the position of which is periodically moved by actuating the piezo element over a distance which is longer than the wavelength of the partial beam. If the period of this process is shorter than the time resolution in registering the fluorescence light emitted because of the multiple photon excitation, the intensity distribution of the interference pattern in the measuring plane is averaged but the general advantage of the non uniform intensity distribution of the interference pattern in multiple photon excitation is nevertheless retained.

The present invention does not relate to a new way of registering or observing fluorescence light emitted by a sample. However, it is clear, that those skilled in the art will provide corresponding known method steps and corresponding known equipment for detecting the fluorescence light. These include, for example, an electronic camera such as a CCD- or CMOS-camera, or one or more photo multipliers. In a preferred embodiment such a photo multiplier is assigned to each of the micro lenses of the micro lens array, the arrangement of the micro lenses being fixed with regard to the photo multipliers, and the sample being scanned, for example, by means of an Galvano mirror or by moving the sample itself.

Other features and advantages of the present invention will become apparent to one with skill in the art upon examination of the following drawings and the detailed description. It is intended that all such additional features and advantages be included herein within the scope of the present invention, as defined by the claims.

BRIEF DESCRIPTION OF THE DRAWINGS

The invention can be better understood with reference to the following drawings. The components in the drawings are not necessarily to scale, emphasis instead being placed upon clearly illustrating the principles of the present invention. In the drawings, like reference numerals designate corresponding parts throughout the several views.

DETAILED DESCRIPTION

Figure 1:
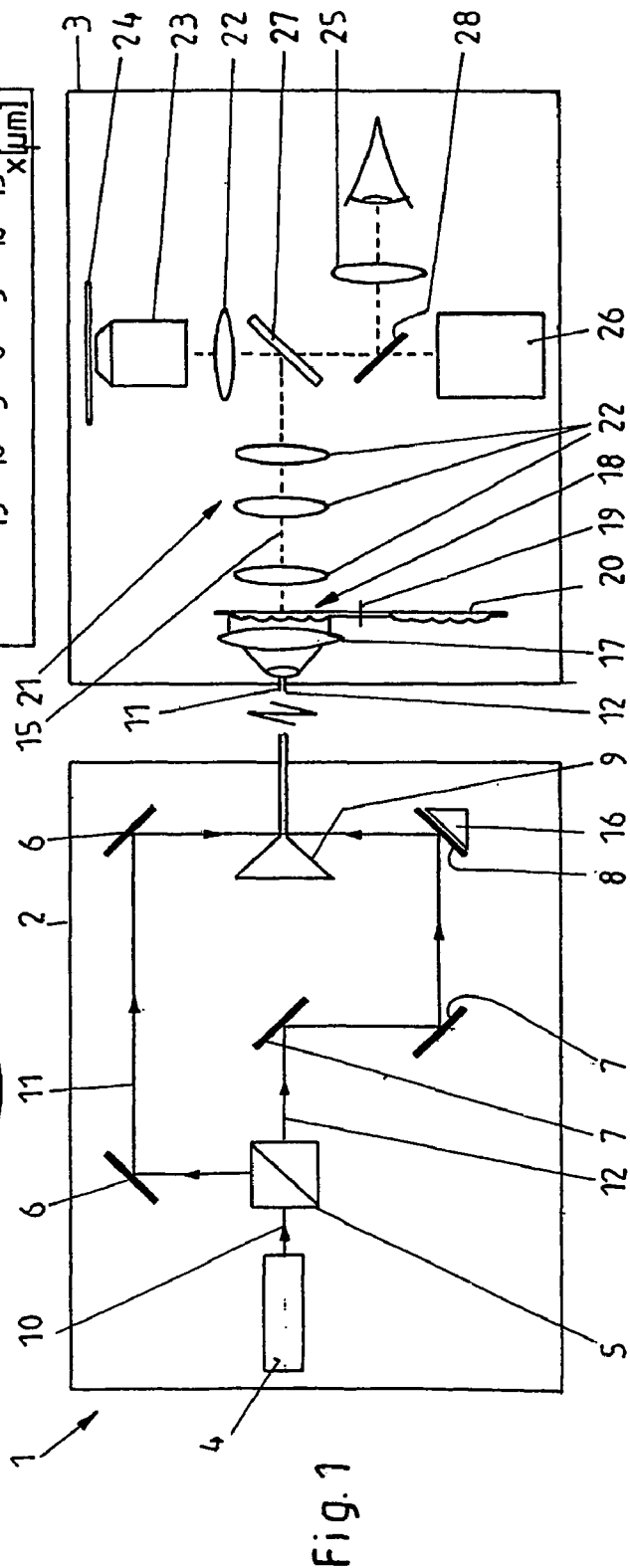
FIG. 1 shows the construction of the new device.

Referring now in greater detail to the drawings, the device 1 shown in FIG. 1 consists of two partial arrangements 2 and 3, the areas of which are each enclosed by a line in the present drawing. This does, however, not mean that the partial arrangements 2 and 3 have to be placed in different housings, or that there has to be another spatial or physical separation. The subdivision of the device 1 into the partial arrangements 2 and 3 only relates to their function.

The partial arrangements 2 of the device 1 includes a laser 4, a beam splitter 5, deviation mirrors 6, 7 and 8, and a roof mirror 9. The laser 4 emits a coherent laser beam 10. The beam splitter 5 splits the laser beam 10 into two partial beams 11 and 12 which are coherent with regard to each other and which each have a same intensity distribution about their beam axes. The partial beams 11 und 12 are deviated by means of the deviation mirrors 6 to 8, and they are directed towards the roof ridge 13 of the roof mirror 9 from different directions. By the roof mirror 9 they are each deviated in such a way that they again run along a common optical axis 15 besides of an inclination angle 14 between their beam axes. In detail, the deviation mirrors 6 are provided for deviating the partial beam 11, and the deviation mirrors 7 and 8 are provided for deviating the partial beam 12. The path lengths of both partial beams between the beam splitter 5 and the roof mirror 9 are of equal length. Accordingly, the partial beams are suitable for interference behind the roof mirror 9. Interference patterns resulting here can be varied by means of operating an piezo element 16 which is supporting the deviation mirror 8 in the optical path of the partial beam 12, because a variation of the path length of the partial beams 12 corresponds to a phase shift as compared to the partial beam 11. The angle 14 between the partial beams 11 and 12 behind the roof mirror 9 is $8{,}4*10^{-4}$ here.

In the partial arrangement 3 of the device 1, the incident partial beams 11 and 12 are formed as follows by means of a lens system 21, which consists of a telescope 17, a micro lens array 18, a plurality of lenses 22 and an oil objective 23. First, the partial beams 11 and 12 are each expanded by the telescope 17. Then the expanded partial beams 11 and 12 reach the micro lens array 18, which is formed by a micro lens disk 20 rotating about an axis 19. The micro lens array 18 focuses each of the partial beams 11 and 12 into a plurality of focus points which are then projected into different measuring points in a measuring plane within a sample 24 via the lenses 22 and the oil objective 23. The intensity distributions of the partial beams 11 and 12 overlap in each measuring point in such a way that their offset with regard to each other is only about 20% of the FWHM of their respective intensity distributions. The inclination angle 14 between the partial beams 11 and 12 results in a formation of an interference pattern extending over the single measuring points in the measuring plane, the type of interference, i.e. destructive or constructive, being dependent on the relative phase and thus on the operation of the piezo element 16 which support the deviation mirror 8. This will be further explained in context of FIG. 3. There where the partial beams 11 and 12 are superimposed in a constructive way and provide a resulting excitation intensity, the sample 24 is excided in a multi photon excitation, which may be assumed as being a two photon excitation, for emission of fluorescence light. This fluorescence light can be directly viewed via an ocular 25, or it can be registered with an electronic camera 26. To this end, two further beams 27 and 28 are provided in the beam path of the device 1. The mirror 27 is preferably a chromatic beam splitter which deviates the partial beams 11 and 12 towards the sample 24 but which allows for transmission of the fluorescence light from the sample towards the ocular 25 and the camera 26, respectively, thus using the different wave length of the partial beams 11 and 12, on the one hand, and of the fluorescence light, of the other light. Even in addition to the mirror 27 being a chromatic beam splitter, a filter which is not depicted here may be arranged in the beam path running towards the camera 26 or the ocular 25, to absorb laser light reflected by the sample 24 for enhancing the signal to background ratio or for protecting the eyes. The mirror 28 can be a semi transmitting mirror. Preferably, however, it is a full reflecting mirror which can be pushed or tilted into the beam path to either observe the sample with the electronic camera 26 or to view it through the ocular 25 each time making use of the full intensity of the fluorescence light.

Figure 2:
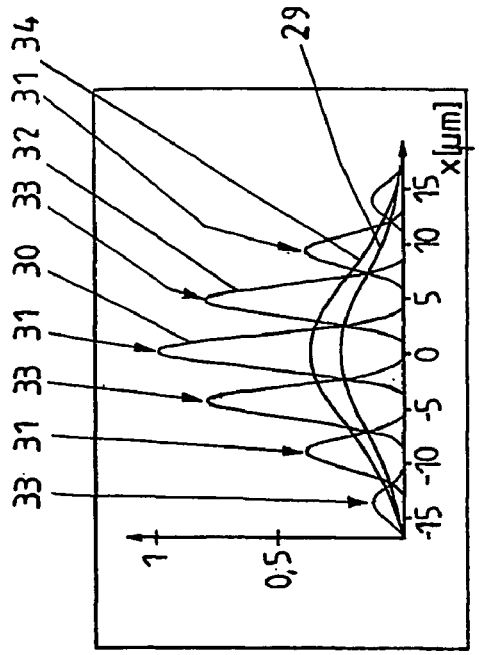
FIG. 2 shows a detail of the device according to FIG. 1.
Figure 3:
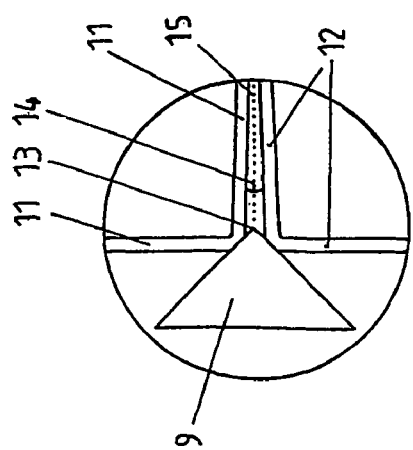
FIG. 3 shows intensity distributions of excitation light over a cross section through the measuring plane in the device according to FIG. 1 as a result of theoretic considerations.

FIG. 3 shows the excitation of the sample for emission of fluorescence light plotted over the position in the sample, i.e. over a cross section through the measuring plane along which the single measuring points are arranged. The cross section through the measuring plane depicted in FIG. 3 is scanned by the micro lens array 18 rotating about the axis 19. In FIG. 3, a curve 29 shows the intensity distribution of the two photon excitation, which would result without dividing up the laser beam 10 into the partial beams 11 and 12. It is a Gaussian intensity distribution. In contrast, the curve 30 shows a constructive superposition in the middle of the overlapping of the partial beams 11 and 12. This results in three areas 31 of maximum intensity arranged side by side between which the excitation of fluorescence light goes down to zero. The curve 32 shows a case of destructive interference in the middle of both intensity distributions. Correspondingly, the fluorescence excitation in the areas 31 of the curve 30 goes down to zero. Instead, areas 33 of maximum intensity are formed in between. If an average is calculated for the curves 30 and 32 and all other possible relative phases of the partial beams 11 and 12, this results in the curve 34 for the fluorescence excitation of the sample 24. The curve 34 corresponds, for example, to measuring the fluorescence with a smaller time resolution than a periodic vibration of the piezoelement 16 which supports the deviation mirror 8. As a result of the non-linearity of the multi photon excitation on which the fluorescence is based, the curve 34 is clearly above the curve 29; i.e. because of the interference of both partial beams 11 and 12 in the area of the sample 24, the yield of fluorescence light from a multi photon excitation of the sample is enhanced. In case of a two photon excitation, the yield of fluorescence light should be practically up to 50% higher than in case of a direct use of the laser beam, only because of the interference of the two partial beams. In case of a three photon excitation, the improvement is up to 150%.

Figure 4:
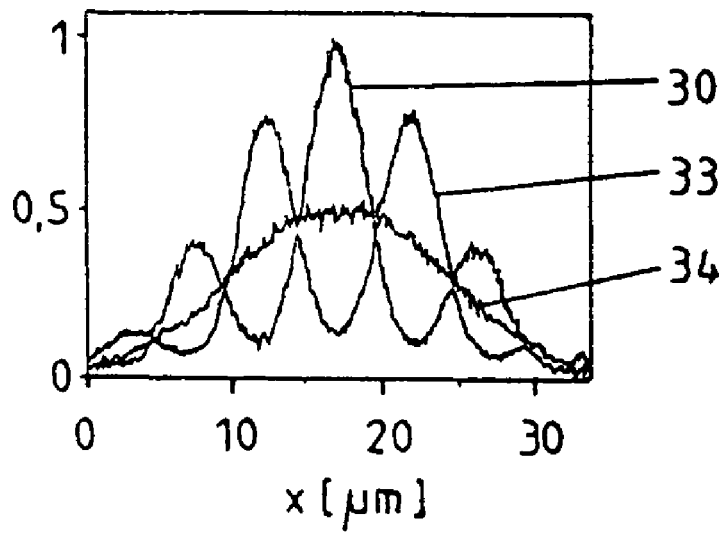
FIG. 4 shows actually measured intensity distributions corresponding to FIG. 3.

The theoretic values depicted in FIG. 3 are confirmed by the measurement values in FIG. 4 which are there represented by the curves 30, 33 and 34. The curve 29 is not depicted in FIG. 4, but it constantly runs below the curve 34 and also has a Gaussian shape.

Figure 5:
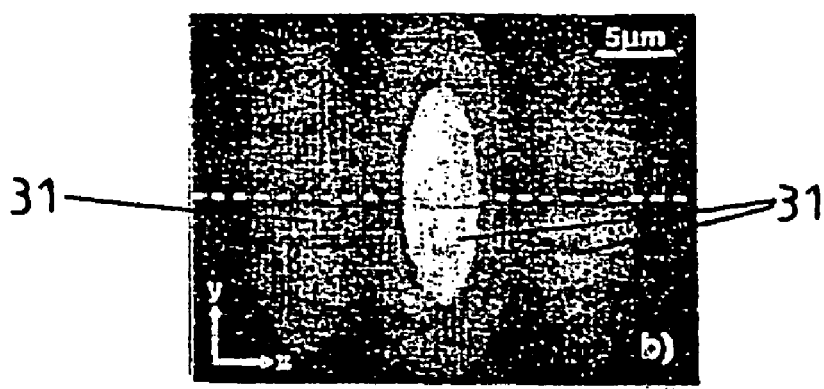
FIG. 5 shows one of the intensity distributions according to FIG. 4 in the measuring plane.
Figure 6:
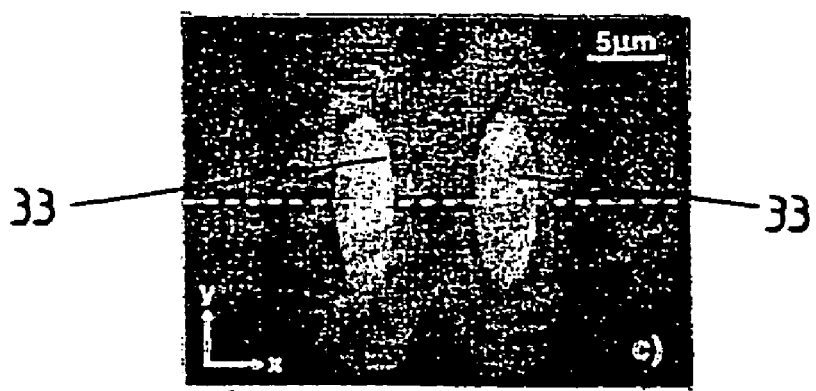
FIG. 6 shows the second intensity distribution according to FIG. 4 in the measuring plane.
Figure 7:
FIG. 7 shows the third intensity distribution according to FIG. 4 in the measuring plane.

FIGS. 5, 6 and 7 show intensity distributions of the excited fluorescence of a homogenous sample arranged in the measurement plane, which correspond to the curves 30, 33 and 34. Whereas FIG. 7 does only report an increase in yield of fluorescence light by means of smearing out the interference patterns of the partial beams 11 and 12, FIGS. 5 and 6 show that the interference pattern also allows for purposefully excite certain areas of a sample stronger than others to, for example, account for different sensitivities of the sample. The interference pattern produced by the partial beams 11 and 12 in the measuring plane is not necessarily comparatively coarse like that one shown in FIGS. 5 and 6. It may also have a higher number of smaller areas of maximum intensity arranged side by side. The general advantages of the new method for multi photon excitation of a sample and of an corresponding device are nevertheless retained. It may even become easier to average the interference patterns over different relative phases. Averaging is a quasi-automatic result, if the interference pattern is finer than the intensity distribution of the partial beams in each measuring point.

Many variations and modifications may be made to the preferred embodiments of the invention without departing substantially from the spirit and principles of the invention. All such modifications and variations are intended to be included herein within the scope of the present invention, as defined by the following claims.

LIST OF REFERENCE NUMERALS

| | |
|---|---|
| 1 | Device |
| 2 | partial arrangement |
| 3 | partial arrangement |
| 4 | laser |
| 5 | beam splitter |
| 6 | deviation mirror |
| 7 | deviation mirror |
| 8 | deviation mirror |
| 9 | roof mirror |
| 10 | laser beam |
| 11 | partial beam |
| 12 | partial beam |
| 13 | roof ridge |
| 14 | inclination angle |
| 15 | optical axis |
| 16 | piezo element |
| 17 | telescope |
| 18 | micro lens array |
| 19 | axis |
| 20 | micro lens wheel |
| 21 | lens system |
| 22 | Lens |
| 23 | Objective |
| 24 | Sample |
| 25 | Ocular |
| 26 | Camera |
| 27 | Mirror |
| 28 | Mirror |
| 29 | Curve |
| 30 | Curve |
| 31 | area |
| 32 | curve |
| 33 | area |
| 34 | curve |

I claim:

1. A method for multi photon excitation of a sample for emission of fluorescence light, comprising the steps of
splitting a laser beam into at least two coherent partial beams each having a beam axis and a same intensity distribution about its beam axis;
directing the partial beams from different directions towards a common measuring plane running transversely to the beam axes at an inclination angle <1 between the beam axes of the partial beams;
projecting the partial beams onto the measuring plane by means of a common lens system, an interference pattern formed by the coherent partial beams within the measuring plane providing areas of maximum light intensity adjacent to areas of minimum light intensity; and
registering the fluorescence light emitted by the sample.

2. The method of claim 1, wherein a lateral offset of the partial beams in the measurement plane caused by the inclination angle is smaller than 50% of a full width at half-maximum (FWHM) of an intensity distribution of each partial beam in the measuring plane.

3. The method of claim 2, wherein the lateral offset of the partial beams in the measurement plane caused by the inclination angle is at maximum 25% of the full width at half-maximum (FWHM) of the intensity distribution of each partial beam in the measuring plane.

4. The method of claim 1, wherein the partial beams are focused in at least one common measuring point within the measuring plane.

5. The method of claim 1, wherein a phase of at least one of the partial beams is modulated by varying a path length of the respective partial beam so that the areas of maximum intensity of the interference pattern are moved forth and back in the measuring plane.

6. The method of claim 4, wherein the partial beams are focused in a plurality of measuring points which are arranged side by side in the measuring plane at the same time, the partial beams interfering with each other in all of these measuring points.

7. The method of claim 6, wherein a distance of the areas of maximum light intensity in the interference pattern is at least half as wide as a distance of the measuring points.

8. A device for multi photon excitation of a sample for emission of fluorescence light comprising:
a laser providing a laser beam;
a beam splitter splitting a laser beam into at least two coherent partial beams each having a beam axis and a same intensity distribution about its beam axis;
beam directing means directing the partial beams from different directions towards a common measuring plane running transversely to the beam axes at an inclination angle <1 between the beam axes of the partial beams;
a common lens system projecting the partial beams onto the measuring plane, an interference pattern formed by the coherent partial beams within the measuring plane providing areas of maximum light intensity adjacent to areas of minimum light intensity; and
a registering unit registering the fluorescence light emitted by the sample.

9. The device of claim 8, wherein the beam directing means include a roof mirror joining the partial beams which are directed towards the roof mirror from opposite directions at its roof ridge.

10. The device of claim 8, wherein the beam directing means include a deviation element modulating a phase of at least one of the partial beams by varying a path length of the respective partial beam.

11. The device of claim 8, wherein the lens system includes a micro lens array made of a plurality of micro lenses arranged side by side in one plane for focusing the partial beams in a plurality of measuring points which are arranged side by side in the measuring plane at the same time, the partial beams interfering with each other in all of these measuring points.

12. The device of claim 11, wherein the inclination angle is smaller than Lambda (M*NA*f), Lambda being the wavelength of the laser beam and the partial beams, M being the magnification upon focusing the partial beams into each measuring point, NA being the numeric aperture of the lens systems, and f being the focal length of each micro lens of the micro lens array.

* * * * *